United States Patent [19]

Chan et al.

[11] Patent Number: 5,474,578
[45] Date of Patent: Dec. 12, 1995

[54] ERASABLE HAIR DYEING PROCESS

[75] Inventors: Alexander C. Chan, Buffalo Grove, Ill.; Alice A. Mayer, Bethel, Conn.; Jia-Shen Wang, New Canaan, Conn.; Gottfried Wenke, Woodbridge, Conn.; Mu-Ill Lim, Trumbull, Conn.

[73] Assignee: Clairol, Inc., New York, N.Y.

[21] Appl. No.: 316,750

[22] Filed: Oct. 3, 1994

[51] Int. Cl.$^6$ ............................................. A61K 7/13
[52] U.S. Cl. ........................ 8/431; 8/405; 8/426; 8/565; 8/574; 8/654; 8/655; 8/657; 8/658; 8/659
[58] Field of Search .................. 8/405, 431, 426, 8/403, 644, 654, 655, 657, 658, 659, 565, 574

[56] References Cited

U.S. PATENT DOCUMENTS

| | | | |
|---|---|---|---|
| 3,482,923 | 12/1969 | Boosen et al. | 8/426 |
| 3,630,655 | 12/1971 | Berth et al. | 8/423 |
| 3,840,338 | 10/1974 | Zviak et al. | 8/426 |
| 3,973,901 | 8/1976 | Micchelli et al. | 8/10.1 |
| 4,170,669 | 10/1979 | Okada | 427/275 |
| 4,452,603 | 6/1984 | Konrad et al. | 8/406 |
| 4,681,471 | 7/1987 | Hayduchok et al. | 106/22 |
| 4,877,411 | 10/1989 | Hines et al. | 8/403 |
| 5,067,966 | 11/1991 | Mager et al. | 8/405 |
| 5,232,494 | 8/1993 | Miller et al. | 106/22 B |
| 5,334,965 | 8/1993 | Clausen et al. | 8/406 |
| 5,380,340 | 1/1995 | Neunhoeffer et al. | 8/405 |

FOREIGN PATENT DOCUMENTS 51-25780  8/1976  Japan.

OTHER PUBLICATIONS

*Dyes and Pigments*, "Photofading of Basic Triphenylmethane Dyes: Evidence for Electron Transfer", 1981, pp. 31–35, Allen et al.

Primary Examiner—Christine Skane
Assistant Examiner—Caroline L. Dusheck
Attorney, Agent, or Firm—Morton S. Simon

[57] ABSTRACT

A hair fiber having a first color is contacted with a dye having the formula I, formula II, formula III or a mixture thereof whereby the fiber has imparted to it a second color, upon subsequent contact with alkaline peroxide the visual appearance of the first color is restored to the fiber.

11 Claims, No Drawings

ERASABLE HAIR DYEING PROCESS

In the consumer market, materials used for temporary hair dye products are composed largely of anionic dyes and cationic surfactants. Anionic dyes and cationic surfactants form insoluble complexes. The insoluble complexes are dispersed in surfactant containing formulations. Because these insoluble complexes have very low affinity to hair they are applied to, and allowed to dry on, the hair fibers without rinsing and shampooing. This can give a coated stiff feel to the dyed hair. Moreover, slight to severe rub-off of the dye complexes often occurs. Additionally, even though manufactures claim that their temporary colors can be removed by one shampooing, residual color on the hair is usually observable even after several shampooings. Examples of prior art efforts to resolve these problems are:

U.S. Pat. No. 3,973,901, which discloses a hair dyeing composition containing water soluble cationic polymers. Patentees suggest the use of different classes of acid dyes, including triarylmethanes substituted with an acidic group, for the temporary dyeing of hair.

German 3,842,774 Cl and U.S. Pat. No. 4,681,471, which teach the use of reducing agents for the decolorization of triarylmethanes. However, the processes of these patents are however, disadvantageous in that they do not completely remove the color from the hair.

U.S. Pat. No. 4,877,411, which discloses a method for temporary coloration of textile materials. The method involves applying to textile material an amine-reducible tint so as to color the textile material. The colored textile material is then contacted with an amine compound to reduce the tint and remove the color from the material. Patentees do not employ alkaline peroxide. More importantly, there are substantial structural differences between the amine-reducible tint employed by patentees and the dyes employed in the present invention.

U.S. Pat. No. 5,232,494, which teaches certain dyes and discloses that hydrogen peroxide can remove them from paper. However, it is well known to those skilled in the art, that dyes do not necessarily behave on hair fibers the way they behave on paper. There is no predictability.

The hair dye art has need of a new temporary hair dye system which can overcome the heretofore discussed problems encountered with temporary hair dye products. Preferably such new temporary hair dye system should permit shampooing of the hair shampooed immediately after it is dyed so that rub-off and the undesirable coated feel of the hair fibers are reduced. Such a system should, by means of a simple treatment, permit removal of the temporary color from the hair. We have found that specific triarylmethane and cyanine dyes fulfill these requirements.

Allen et al (*Dyes and Pigments;* 198 1; 2, 3 1.) propose that triarylmethane fading may be due to a reaction between the dye and hydrogen peroxide. Allen et al specify the triarylmethanes that will react with hydrogen peroxide and suggest that hydrogen peroxide will react with any triarylmethane. Surprisingly and unexpectedly, we have found that only triarylmethanes of the general formula I of the present invention will readily react with hydrogen peroxide to form colorless products. We have also discovered that to efficiently decolorize the dye, the dyed hair must be treated with hydrogen peroxide at an alkaline pH. This is wholly unappreciated by the prior art. Moreover, Allen et al are concerned with the use of triarylmethanes to dye cotton and acrylic materials. In contradistinction thereto, the present invention is concerned with the use of certain triarylmethane compounds of formula I to dye keratin fibers, particularly human hair. Those skilled in the hair dye art are aware that compounds that can be used to dye cotton and acrylic fibers are not necessarily useful for dyeing human hair. There is no predictability.

As noted heretofore, we have found that certain dyestuffs can be advantageously employed in a system for temporarily coloring a keratin fiber, such as a hair fiber. Such a system is hereinafter referred to as an erasable dye system. The dyestuff that can be used in the system of the present invention is selected from the group consisting of compounds of the following general formulas I, II and III:

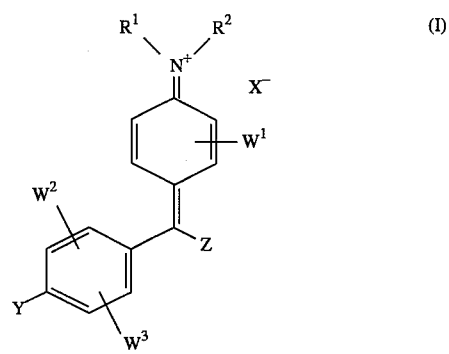
(I)

wherein, Z is:

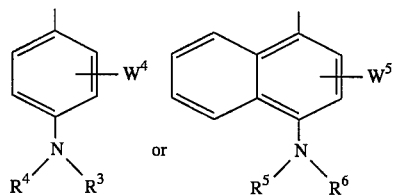

; $R^1$, $R^2$, $R^3$, $R^4$, $R^5$, $R^6$, $W^1$, $W^2$, $W^3$, $W^4$ and $W^5$ are, independently, hydrogen, halogen, $C_1$–$C_4$ alkyl or $C_1$–$C_4$ hydroxyalkyl; Y hydrogen or

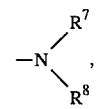

wherein $R^7$ and $R^8$ are, independently, hydrogen, halogen, $C_1$–$C_4$ alkyl or $C_1$–$C_4$ hydroxyalkyl; and X is a cosmetically acceptable counter anion;

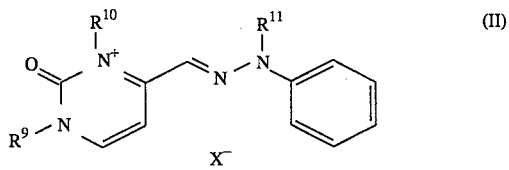
(II)

wherein, $R^9$ and $R^{10}$ are, independently, $C_1$–$C_4$ alkyl or $C_1$–C4 hydroxyalkyl; $R^{11}$ is hydrogen, $C_1$–$C_4$ alkyl or $C_1$–$C_4$ hydroxyalkyl; and X is as previously defined; and

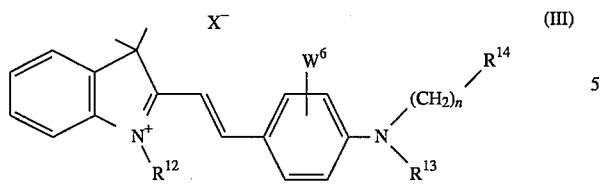

(III)

wherein, $R^{12}$ is $C_1$–$C_4$ alkyl or $C_1$–$C_4$ hydroxyalkyl; $R^{13}$ and $W^6$ are, independently, hydrogen, $C_1$–$C_4$ alkyl or $C_1$–$C_4$ hydroxyalkyl; $R^{14}$ is cyano or halogen; n is 1 or 2; and X is as previously defined.

Mixtures of two or more compounds of the formulas I, II and III may be employed. In each of general formulas I, II and III, counter anion X is, preferably, halide, acetate, sulfate, methylsulfate, nitrate or oxalate.

The erasable dye system of the present invention employs: (1) a dye composition comprising a tinctorially-effective amount of a dyestuff of formula I, II or III, in a cosmetically acceptable vehicle; and (2) an erasing composition comprising an oxidizing agent, preferably, hydrogen peroxide, more preferably, alkaline hydrogen peroxide, in a cosmetically acceptable vehicle. The erasable dye system may optionally contain as a third component (3) a bisulfite solution. More importantly, the erasable dye system of the present invention permits the original color of the dyed hair to be restored by a simple treatment with hydrogen peroxide, followed by an optional treatment with bisulfite solution.

The erasable dye system of the present invention imparts a color to hair which is resistant to shampooing. This eliminates the color rub-off problem which is common to all commercially available temporary hair colors.

More specifically, the present invention provides an erasable dye system for keratin fibers having a first color, said system comprising:

(a) a dye composition containing
  (1) an amount of a dye compound selected from the group consisting of:

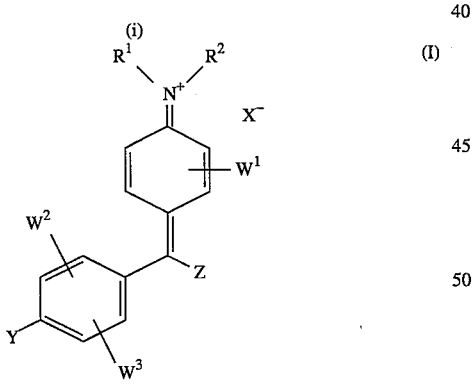

(I)

wherein, Z is:

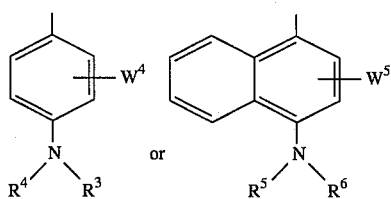

; $R^1$, $R^2$, $R^3$, $R^4$, $R^5$, $R^6$, $W^1$, $W^2$, $W^3$, $W^4$ and $W^5$ are, independently, hydrogen, halogen, $C_1$–$C_4$ alkyl or $C_1$–$C_4$ hydroxyalkyl; Y hydrogen or

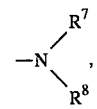

wherein $R^7$ and $R^8$ are, independently, hydrogen, halogen, $C_1$–$C_4$ alkyl or $C_1$–$C_4$ hydroxyalkyl; and X is a cosmetically acceptable counter anion;

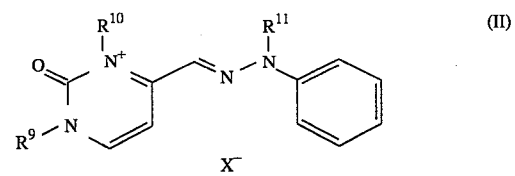

(II)

wherein $R^9$ and $R^{10}$ are, independently, $C_1$–$C_4$ alkyl or $C_1$–$C_4$ hydroxyalkyl; $R^{11}$ is hydrogen, $C_1$–$C_4$ alkyl or $C_1$–$C_4$ hydroxyalkyl; and X is as previously defined;

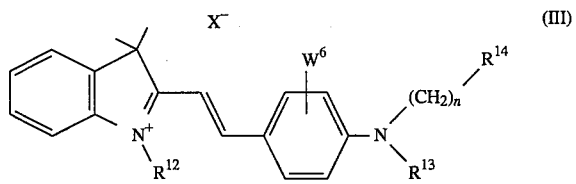

(III)

wherein $R^{12}$ is $C_1$–$C_4$ alkyl or $C_1$–$C_4$ hydroxyalkyl; $R^{13}$ and $W^6$ are, independently, hydrogen, $C_1$–$C_4$ alkyl or $C_1$–$C_4$ hydroxyalkyl; $R^{14}$ is cyano or halogen; n is 1 or 2; and X is as previously defined; and
(iv) mixtures thereof;
the dye compound being present in the dye composition in an amount sufficient to color the keratin fibers a second color when the keratin fibers are contacted with the composition and
(2) a cosmetically acceptable vehicle for the dye compound;

(b) an erasing composition containing alkaline hydrogen peroxide in an amount sufficient to remove a sufficient amount of the dye compound from keratin fibers having the second color due to contact with the dye composition so that such keratin fibers appear to have had the first color restored thereto; and (c) indicia instructing that (i) the first dye composition be applied to keratin fibers having the first color so that the second color is imparted thereto; and (ii) when it is desired to restore the appearance of the first color to the keratin fibers having the second color, the keratin fibers having the second color be contacted with the erasing composition for a time sufficient to restore to such keratin fibers the appearance of the first color.

The following examples are offered to illustrate the present invention and not for the purpose of limiting same. It should be noted that unless indicated to the contrary, all percentages are by weight and are based on the total weight of the composition.

EXAMPLE 1

A swatch of blended gray hair was treated for 10 minutes with the following composition.

| | |
|---|---|
| Ethyl alcohol | 45.125% |
| New Fuchsin | 0.03% |
| Water q.s. | 100% |

New Fuchsin is a compound of formula I having the structure:

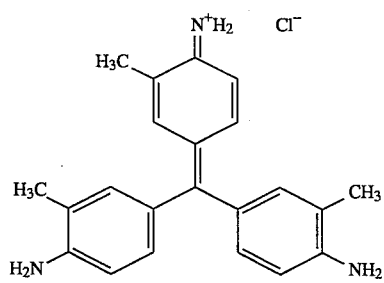

The treated swatch was then shampooed. A violet color was imparted to the hair fibers. The shampooed dyed swatch was treated for 5 minutes with alkaline 3% hydrogen peroxide solution (pH 9.5). The violet color was removed and the original color of the hair was restored.

Tristimulus values of the hair were determined for the undyed hair, after dyeing and after treatment with alkaline peroxide. The results are set forth in Table 1, below.

TABLE 1

| | L | a | b | x | % removal |
|---|---|---|---|---|---|
| Initial reading of undyed hair | 35.2 | 0.3 | 6.6 | | |
| After dyeing | 28.8 | 13.0 | 0.5 | 15.5 | |
| After treatment with alkaline peroxide (pH 9.5) | 34.4 | 1.7 | 6.7 | 1.6 | 90 |

It should be noted that in Table 1, X represents the total color difference between the undyed swatch and the treated swatch. It is calculated by the equation:

$$x = \sqrt{(L_i - L_o)^2 + (a_i - a_o)^2 + (b_i - b_o)^2}$$

where $L_o$, $a_o$ and $b_o$ are tristimulus values of the undyed hair and $L_i$, $a_i$ and $b_i$ are the values of the treated hair. The percentage of color removal was calculated as follows:

% removal=[1−(X after alkaline peroxide treatment/X after dyeing)]×100.

EXAMPLE 2

A swatch of commercially bleached hair was treated for 10 minutes with the following composition.

| | |
|---|---|
| Ethyl alcohol | 45.125% |
| Brilliant Green | 0.03% |
| Water q.s. | 100% |

Brilliant Green is a compound of formula I having the structure:

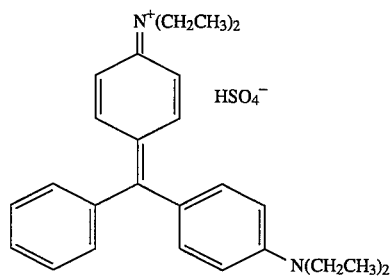

The treated swatch was then shampooed. A green color was imported to the hair fibers. The shampooed dyed swatch was treated for 5 minutes with alkaline 3% hydrogen peroxide solution (pH 9.5). This effected a significant removal of the green color. For a more satisfying result, the swatch was further treated for an additional 2 minutes with a solution which contained 15.56% ammonium bisulfite and had a neutral pH. As a consequence, the white color of the hair was restored.

Tristimulus values of the hair were determined for the undyed hair, after dyeing and after treatment with peroxide and reducing agent. The results are set forth in Table 2 below.

TABLE 2

| | L | a | b | X | % removal |
|---|---|---|---|---|---|
| Initial reading of undyed hair | 66.5 | −1.6 | 17.6 | | |
| After dyeing | 43.8 | −25.5 | −1.0 | 37.8 | |
| After treatment with alkaline peroxide (pH 9.5) and subsequent treatment with reducing agent | 64.3 | −2.9 | 17.1 | 2.6 | 93 |

EXAMPLE 3

A swatch of blended gray hair was treated for 30 minutes with the following composition.

| | |
|---|---|
| Hydroxyethylcellulose | 0.5% |
| Ethyl alcohol | 4.75% |
| Triethylamine | 1.5% |
| Basic Violet 14 | 0.5% |
| Victoria Pure Blue | 0.5% |
| Water q.s. | 100% |

Basic Violet 14 is a compound of formula I having the structure:

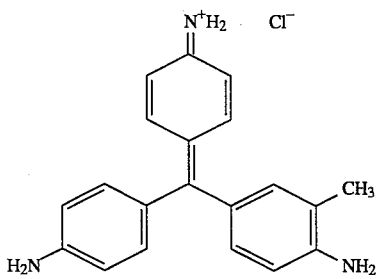

Victoria Pure Blue is a compound of formula I having the structure:

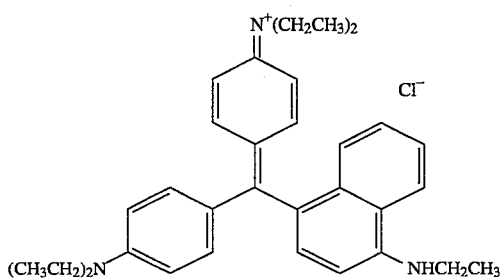

The treated swatch was then shampooed. A red violet color was imparted to the hair fibers. The shampooed dyed swatch was treated for 10 minutes with alkaline 3% hydrogen peroxide solution (pH 9.5). All of the color was essentially removed and the original color of the hair was restored.

EXAMPLE 4

Two swatches of light gray hair were treated for 15 minutes with the following composition.

| | |
|---|---|
| Basic Blue 1 | 0.05% |
| Ethyl alcohol | 2.375% |
| Monoethanolamine | q.s. pH 7.8 |
| Water | q.s. 100% |

Basic Blue is a compound of formula I having the structure:

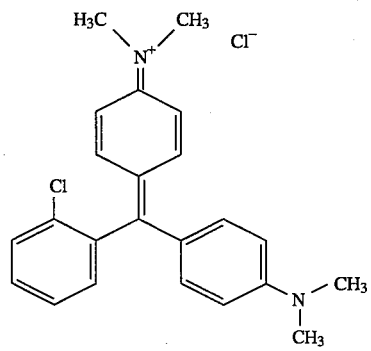

The treated swatches were then shampooed. The hair fibers of the shampooed swatches were imparted a greenish blue color. Then, to illustrate the impact of pH on the color removal process, one of the dyed swatches was treated for 5 minutes with alkaline 6% hydrogen peroxide (pH 9.5), and the other was treated for 5 minutes with acidic 6% hydrogen peroxide (pH 5). A significant difference between the two swatches was observed. Much more color was removed from the swatch post-treated with the alkaline peroxide solution. A further 3 minutes treatment of the first swatch with fresh alkaline 6% peroxide solution (pH 9.5) resulted in almost complete restoration of the original hair color. On the other hand, an intense color was still observable on the second swatch even after it was subjected to an additional 3 minutes of treatment with fresh acidic 6% peroxide solution (pH 5).

Tristimulus values of the hair were determined for the undyed hair, after dyeing, after the 5 minute treatment with peroxide and after the further 3 minute treatment with peroxide. The results are set forth in Table 3 below.

TABLE 3

| | L | a | b | x | % removal |
|---|---|---|---|---|---|
| Initial reading of undyed hair | 41.4 | −0.5 | 7.1 | | |
| 1st swatch: | | | | | |
| After dyeing | 27.3 | −12.5 | −7.7 | 23.7 | |
| After 5 min. treatment with alkaline peroxide (pH 9.5) | 41.3 | −3.9 | 5.5 | 3.8 | 84 |
| After 3 more min. of alkaline peroxide treatment (pH 9.5) | 43.3 | −1.3 | 7.4 | 2.1 | 91 |
| 2nd swatch: | | | | | |
| After dyeing | 27.8 | −12.0 | −6.6 | 22.5 | |
| After 5 min. treatment with acidic peroxide (pH 5) | 30.4 | −11.6 | −4.5 | 19.5 | 13 |
| After 3 more min. of acidic peroxide treatment (pH 5) | 31.4 | −10.9 | −2.7 | 17.4 | 23 |

Examples 5 to 7, which follow, serve to demonstrate that not all triarylmethanes are useful in the erasable dye system of the present invention.

EXAMPLE 5

A swatch of blended gray hair was treated for 10 minutes with the following composition.

| | |
|---|---|
| Ethyl alcohol | 45.125% |
| Rosolic Acid | 0.03% |
| Water q.s. | 100% |

Rosolic acid has the structure:

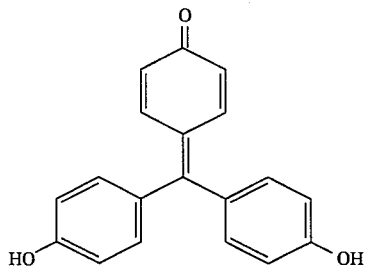

The treated swatch was then shampooed. A yellow color was imparted to the hair fibers. The shampooed dyed swatch was treated for 5 minutes with alkaline 3% hydrogen peroxide solution (pH 9.5). The original color could not be restored. Thus, it is clear that not all triarylmethanes can be decolorized by alkaline hydrogen peroxide.

Tristimulus values of the hair were determined for the undyed hair, after dyeing and after treatment with alkaline peroxide. The results are set forth in Table 4 below.

TABLE 4

|  | L | a | b | x | % removal |
|---|---|---|---|---|---|
| Initial reading of undyed hair | 35.1 | 0.0 | 6.7 | | |
| After dyeing | 31.9 | 3.6 | 10.0 | 5.8 | |
| After treatment with alkaline 3% peroxide (pH 9.5) | 33.0 | 2.7 | 7.7 | 3.6 | 38 |

EXAMPLE 6

A swatch of bleached hair was treated for 15 minutes with the following composition.

| Ammonium lauryl sulfate | 6.0% |
|---|---|
| 2,2,4-trimethyl-1,3-pentanediol | 4.0% |
| Citric acid | 1.0% |
| Hydroxyethylcellulose | 3.0% |
| Coomassie Brilliant Blue | 0.5% |
| Water q.s. | 100% |

Coomassie Brilliant Blue has the structure:

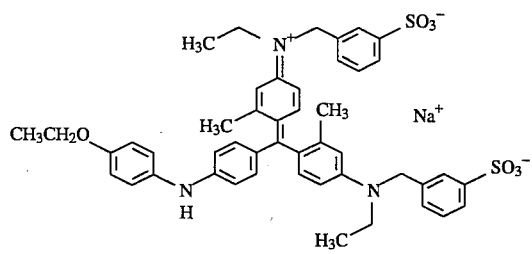

The treated swatch was then shampooed. A greenish blue color was imparted to the hair fibers. The shampooed dyed swatch was treated for 5 minutes with alkaline 3% hydrogen peroxide solution (pH 9.5). The swatch was then treated for an additional 2 minutes with an aqueous 15.56% ammonium bisulfite solution having a neutral pH.

Tristimulus values of the hair were determined for the undyed hair, after dyeing, after treatment with the peroxide and after treatment with the reducing agent. The results are set forth in Table 5, below.

TABLE 5

|  | L | a | b | x | % removal |
|---|---|---|---|---|---|
| Initial reading of undyed hair | 59.7 | 1.4 | 14.3 | | |
| After dyeing | 42.5 | −10.1 | 4.8 | 22.8 | |
| After treatment with alkaline peroxide (pH 9.5) | 48.3 | −8.7 | 3.1 | 18.9 | 17.1 |
| After subsequent treatment with reducing agent | 43.0 | −2.2 | 6.2 | 18.9 | 17.1 |

It is obvious from the results reported in Table 5, that the alkaline peroxide treatment, whether alone or in combination with the post-treatment with the reducing agent, did not remove sufficient color from the hair to restore the appearance of the original color.

EXAMPLE 7

A swatch of blended gray hair was treated for 10 minutes with the following composition.

| Hydroxyethylcellulose | 0.5% |
|---|---|
| Ethyl alcohol | 4.75% |
| Triethylamine | 1.5% |
| Cresol Red | 0.5% |
| Bromophenol Blue | 0.5% |
| Water qs | 100% |

Cresol Red has the structure:

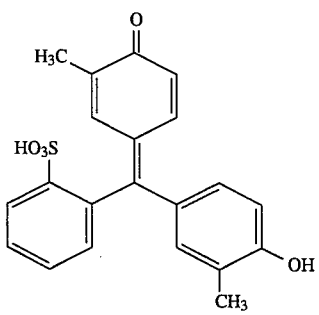

Bromophenol Blue has the structure:

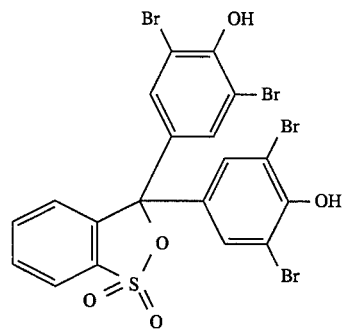

The treated swatch was then shampooed. A green color was imparted to the hair fibers. The shampooed dyed tress was then treated for 5 minutes with an alkaline 3% hydrogen peroxide solution (pH 9.5). Only part of the color was removed. A significant amount of the dyes still remained on the fibers. The appearance of the original color could not be restored.

EXAMPLE 8

A swatch of blended gray hair was treated for 20 minutes with an acidic (pH 4.1) 0.1% aqueous solution of Basic Red 49. Basic Red 49 is a compound of formula III having the structure:

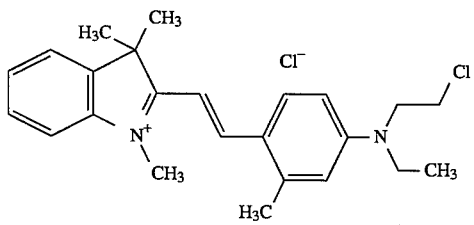

The swatch was dyed then rinsed with water. An orange color was imparted on the hair fibers. The dyed rinsed swatch was then treated for 5 minutes with the following composition:

| | |
|---|---|
| 6% Hydrogen peroxide solution | 75% |
| Green Shampoo | 25% |
| Ammonium hydroxide q.s. pH = 9.9 | |

Most of the color was removed at the end of this treatment.

Tristimulus values of the hair were determined for the undyed hair, after dyeing and after treatment with the alkaline peroxide/shampoo composition. The results are set forth in Table 6, below.

TABLE 6

| | L | a | b | x | % removal |
|---|---|---|---|---|---|
| Initial reading of undyed hair | 32.0 | 0.3 | 6.6 | | |
| After dyeing | 24.6 | 15.2 | −1.0 | 18.3 | |
| After treatment with the alkaline 6% peroxide shampoo composition (pH 9.9) | 34.2 | 2.2 | 6.2 | 2.9 | 84 |

As shown by the Tristimulus values of the swatch at different stages, most of the color was removed by the end of the treatment. Moreover, the hair appeared to have had its original color restored.

To demonstrate that one cannot predict the activity of a dye on hair from its activity on paper, the following Example 9 was carried out.

EXAMPLE 9

A swatch of blended gray hair was treated for 20 minutes with an acidic (pH 4.1) 0.1% aqueous solution of Astrazon Blue FRR (Basic Blue 69), a compound known to be useful for dying paper. The structure of Astrazon Blue FRR is as follows:

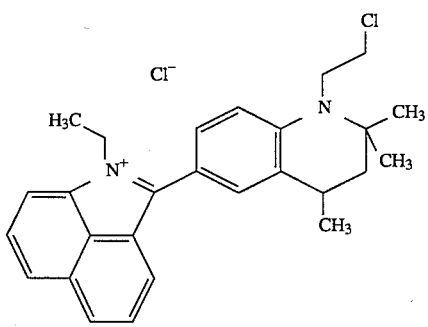

The swatch was then rinsed. A violet color was imparted on the hair fibers. The dyed rinsed swatch was then treated for 5 minutes with the alkaline peroxide/shampoo composition of Example 8. The treatment was not very successful in removing the color.

Tristimulus values of the hair were determined for the undyed hair, after dyeing and after the treatment with the alkaline peroxide/shampoo composition. The results are set forth in Table 7, below.

TABLE 7

| | L | a | b | x | % removal |
|---|---|---|---|---|---|
| Initial reading of undyed hair | 32.0 | 0.3 | 6.6 | | |
| After dyeing | 18.1 | 1.8 | −12.6 | 23.8 | |
| After treatment with the alkaline 6% peroxide/ shampoo composition (pH 9.9) | 28.0 | −1.4 | −4.5 | 11.9 | 50 |
| Control (undyed hair treated with only alkaline 6% peroxide/ shampoo composition (pH 9.9) | 34.8 | 0.7 | 8.0 | | |

U.S. Pat. No. 5,232,494 teaches that Astrazon Blue FRR is erasable from paper. However, the poor removability of this dye from hair demonstrates that one can not predict the action of a dye on hair from the action of the dye on paper.

The results of Table 7, above, in respect of the control indicate that the alkaline 6% peroxide/shampoo treatment may cause some hair bleaching through it may not be visible to the eye. Notwithstanding, treatment time is important. The time of treatment with the alkaline 6% peroxide/ shampoo should be that which is just sufficient to restore the visual appearance of the original color. Preferably this time should not be substantially exceeded. Generally a treatment time of not more than 5 minutes is employed. In order to minimize possible hair bleaching, the treatment time is preferably 1 to 3 minutes. More preferably, a treatment time of 1 to 2 minutes is employed.

EXAMPLE 10

A swatch of blended gray hair was treated for 20 minutes with 0.1% aqueous solution of Basic Yellow 49. Basic Yellow 49 is a compound of formula II. The structure of Basic Yellow 49 is as follows:

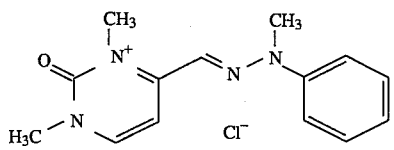

The dyed swatch was rinsed. A yellow color was imparted on the hair fibers. The rinsed dyed swatch was treated for 5 minutes with the alkaline peroxide/shampoo composition of Example 8. The color was readily removed by such treatment and the appearance of the color of the hair before dyeing was restored.

Tristimulus values of the hair were determined for the undyed hair, after dyeing and after the treatment with the alkaline peroxide/shampoo composition. The results are set forth in Table 8, below.

TABLE 8

| | L | a | b | X | % removal |
|---|---|---|---|---|---|
| Initial reading of undyed hair | 32.0 | 0.3 | 6.6 | | |
| After dyeing | 28.9 | 2.2 | 13.8 | 8.1 | |
| After treatment with the alkaline 6% peroxide/shampoo | 32.8 | 0.7 | 8.9 | 2.5 | 70 |

TABLE 8-continued

| | L | a | b | X | % removal |
|---|---|---|---|---|---|
| composition (pH 9.9) | | | | | |

The dye compositions employed in the erasable dye system of the present invention may be formulated as a liquid shampoo (which can be a solution or an emulsion), a cream, a gel, a powder, or an aerosol.

Other temporary dyes and materials known to be useful in direct dye compositions for dyeing hair on a living human head may be incorporated in the erasable direct dye system of the present invention provided such agents do not prevent the erasability of the present dye system. In other words, the added material(s) should not prevent restoration of the visible appearance of the original color of the hair. Moreover, the erasing composition of the present invention may also contain one or more materials typically included in hair dye developers known in the art.

Materials typically included in hair dye compositions and/or developers include for example, organic solvents and solubilizing agents, surface active agents, thickening agents, buffers, chelating agents, perfumes, sunscreens, conditioners, dyeing assistants or penetrating agents, preservatives, emulsifiers and fragrances. A particular material may perform several functions. For example, a surfactant may also act as a thickener. The dye compounds of formulas I, II and III are cationic. The dye uptake of cationic dyes is inhibited by excess anionic material with which the cationic dyes would complex, precipitate or similarly react. Consequently, care should be exercised in formulating with large anions.

It is often advantageous to include in the dye compositions of the present invention an organic solvent or solvent system which helps solubilize the dyes and adjuvants contained in the compositions. A number of organic solvents are known for such purpose. These include: alcohols, particularly alkyl alcohols of 1–6 carbons, especially ethanol and propanol; glycols of up to about 10 carbons, preferably less than 6 carbons, especially propylene glycol and butylene glycol; glycol ethers of up to about 10 carbons, especially diethyleneglycol monobutyl ether; carbitols; and benzyl alcohol. When present, the solvents will constitute from about 1% to about 60%, preferably from about 10 to about 30%, by weight of the dyeing composition.

Typical surfactant types useful in the compositions of the invention include: alkyl sulfates, alkyl ether sulfates, amide ether sulfates, soaps, alkyl ether carboxylates, acylsarcosinates, protein/fatty acid condensates, sulfosuccinic acid esters, alkane sulfonates, alkylbenzene sulfonates, α-olefin sulfonates, acylisethionates, acyltaurines, ethoxylates, sorbitan esters, alkanolamides, amine oxides, quaternary ammonium salts, alkyl betaines, amidopropyl betaines, sulfobetaines, glycinates/aminopropionates and carboxyglycinates/aminodipropionates. A combination of different surfactants can be used to impart particular viscosity and foaming properties.

Illustrative of specific surfactants that may be employed are: lauryl sulfate; polyoxyethylene lauryl ester; myristyl sulfate; glyceryl monostearate; sodium salt of palmitic acid, methyl taurine; cetyl pyridinium chloride; lauryl sulfonate; myristyl sulfonate; lauric diethanolamide; polyoxyethylene stearate; stearyl dimethyl benzyl ammonium chloride; dodecyl benzene sodium sulfonate; nonyl naphthalene sodium sulfonate; dioctyl sodium sulfosuccinate; sodium N-methyl-N-oleyl taurate; oleic acid ester of sodium isethionate; sodium dodecyl sulfate, and the like. The quantity of water soluble surface active agent employed can vary widely up to about 15%. Preferably, the surface active agent is employed in an amount of from about 0.10% to about 10%, based on the weight of the composition. Note however that when an anionic surfactant is employed the amount must be restricted so as to avoid possible incompatibility with the dye compounds of formulas I, II and III.

The thickening agent, when employed, may be one or a mixture of those commonly used in hair dyeing compositions or in hair developers. Such thickening agents include: sodium alginate; gum arabic; cellulose derivatives, such as methylcellulose or the sodium salt of carboxymethylcellulose; acrylic polymers, such as polyacrylic acid sodium salt; and inorganic thickeners, e.g., bentonite and fumed silica. Electrolytes, alkanolamides, cellulose ethers and highly ethoxylated compounds (such as esters, esters and diesters) may also be used to thicken the composition. The quantity of thickening agent can vary over a wide range. Typically the thickening agent(s) is employed in an amount of up to about 20%, more preferably, from about 0.1% to 5%, based on the weight of the composition.

The pH of the dye composition can vary from about 2.5 to about 11. Any compatible water-dispersible alkalizing agent can be incorporated in the composition in an amount suitable to give the desired pH. Typically, the amount of alkalizing agent employed is less than about 10%, preferably, from about 0.1% to about 5%, based on the weight of the composition.

Compatible alkalizing agents are those that do not interact chemically with the dye(s) employed, that do not precipitate the dye(s), and that are non-toxic and non-injurious to the scalp, under the conditions of use. Preferred alkalizing agents include: mono-, di- and trialkanolamines, such as triethanolamine and 2-amino-2-methyl-1,3-propanediol; alkyl amines, such as monoethylamine, diethylamine and dipropylamine; and heterocyclic amines, such as morpholine, piperidine, 2-pipecoline and piperazine.

Any inorganic or organic acid or acid salt, that is compatible with the dye composition and does not introduce toxicity under its conditions of use, can also be employed to adjust the pH of the dye composition. Illustrative of such acids and acid salts are sulfuric acid, formic acid, acetic acid, lactic acid, citric acid, tartaric acid, ammonium sulfate, sodium dihydrogen phosphate, and potassium bisulfate.

Common chelating agents that can be employed in the compositions of the invention include the salts of ethylenediaminetetraacetic acid (EDTA), nitrilotriacetic acid, phosphates, pyrophosphates and zeolites.

Conditioners that can be incorporated in the present compositions include: encapsulated silicones; silicones, such as amino functional and carboxy silicones; volatile silicones; combinations of a cationic polymer, a decomposition derivative of keratin and a salt; quaternary ammonium compounds such as cocos-$(C_{12-18})$-alkyl poly (6) oxyethyl di-(2-lauroyloxyethyl)-methyl ammonium chloride; combinations of a plant extract and a polypeptide; a dimethyl diallyl ammonium chloride (DMDAAC)/acrylic acid type polymer; and a dialkyl quaternary ammonium compound where the alkyl groups are $c_{12}$–$C_{16}$. Other well known conditioners, such as lanolin, glycerol, oleyl alcohol, cetyl alcohol, mineral oil and petrolatum, can also be incorporated.

It is a common practice to add solvents or swelling agents to enhance the penetration of hair dyes. Materials useful for swelling hair include acetic acid, formic acid, formamide, urea, ethyl amine and certain alkali halides (potassium iodide, sodium bromide, lithium bromide and lithium chloride, but not sodium chloride). N-Alkyl pyrrolidones and epoxy pyrrolidone may be employed to potentially increase the penetration of dye into hair. Imidazolines such as disclosed in U.S. Pat. No. 5,030,629 may be employed in the compositions to enhance the penetration of hair dyes.

Emulsifiers may be used when the final form of the hair dye is an emulsion. Many emulsifiers are by their nature also surfactants. Them are five general categories: anionic, cationic, nonionic, fatty acid esters and sorbitan fatty acid esters. Examples include: mono-, dialkyl and trialkyl ether phosphates, long-chain fatty acids with hydrophilic compounds such as glycerin, polyglycerine or sorbitol and long chain alkyl primary and secondary amines, quaternary ammonium and quaternary pyridinium compounds.

Materials which may render the product aesthetically more appealing, such as fragrances, proteins hydrolysates, vitamins and plant extracts, may be added. Examples include chamomile, aloe vera, ginseng, and pro-vitamin B.

What is claimed is:

1. A process for erasably coloring a hair fiber on a living human head, said hair fiber having a first color, said process comprising
   (1) contacting said hair fiber with a composition containing a dye selected from the group consisting of
      (i) dyes having the formula I

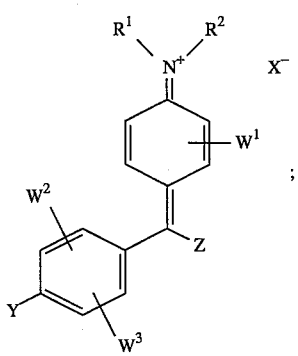

wherein, Z is

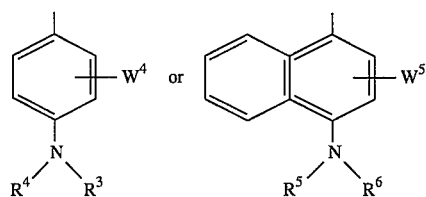

; $R^1$, $R^2$, $R^3$, $R^4$, $R^5$, $R^6$, $W^1$, $W^2$, $W^3$, $W^4$ and $W^5$ are, independently, hydrogen, halogen, $C_1$–$C_4$ alkyl or $C_1$–$C_4$ hydroxyalkyl; Y is hydrogen or

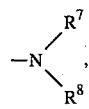

wherein $R^7$ and $R^8$ are, independently, hydrogen, halogen, $C_1$–$C_4$ alkyl or $C_1$–$C_4$ hydroxyalkyl; and X is a cosmetically acceptable counter anion;

(ii) dyes having the formula II

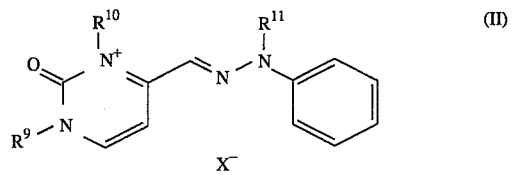

wherein $R^9$ and $R^{10}$ are, independently, $C_1$–$C_4$ alkyl or $C_1$–$C_4$ hydroxyalkyl; $R^{11}$ is hydrogen, $C_1$–$C_4$ alkyl or $C_1$–$C_4$ hydroxyalkyl; and X is as previously defined; and (iii) dyes having the formula III

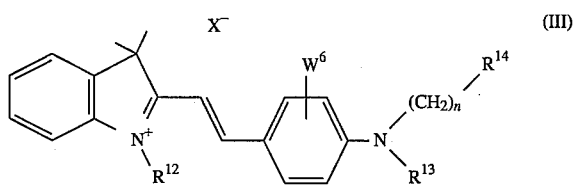

wherein $R^{12}$ is $C_1$–$C_4$ alkyl or $C_1$–$C_4$ hydroxyalkyl; $R^{13}$ and $W^6$ are, independently, hydrogen, $C_1$–$C_4$ alkyl or $C_1$–$C_4$ hydroxyalkyl; $R^{14}$ is cyano or halogen; n is 1 or 2; and X is as previously defined; and (iv) mixtures thereof;

and a cosmetically acceptable vehicle therefor; said dye being present in said composition in an amount sufficient to impart to said hair during said contacting, a second color; and (2) contacting said hair fiber having said second color imparted to it with alkaline hydrogen peroxide in an amount and for a time sufficient to restore to such fiber a visual appearance of said first color.

2. The process as claimed in claim 1, wherein after the hair fiber having the second color imparted to it is contacted with alkaline peroxide it is contacted with a reducing composition containing a cosmetically acceptable salt of a reducing agent and a cosmetically acceptable vehicle therefor.

3. The process as claimed in claim 2, wherein the reducing composition is an aqueous solution of ammonium bisulfite.

4. The process as claimed in claim 1, wherein the dye is

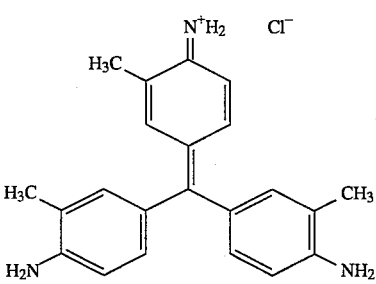

5. The process as claimed in claim 1, wherein the dye is

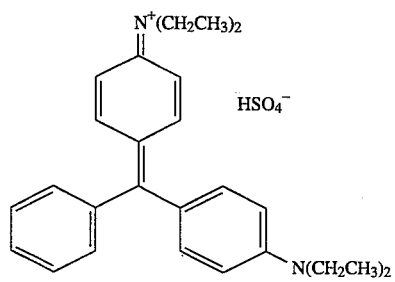
6. The process as claimed in claim 1, wherein the dye is
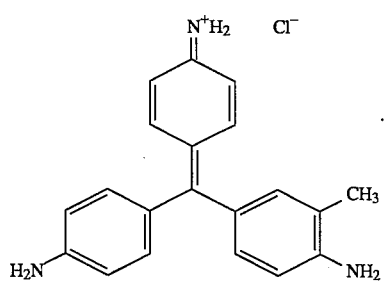
7. The process as claimed in claim 1, wherein the dye is
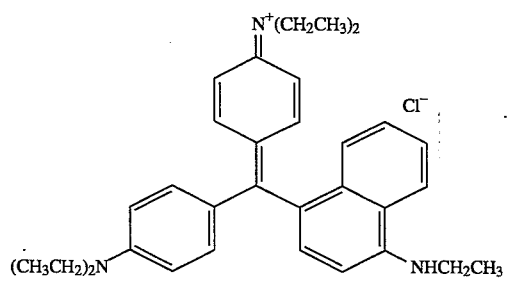
8. The process as claimed in claim 1, wherein the dye is
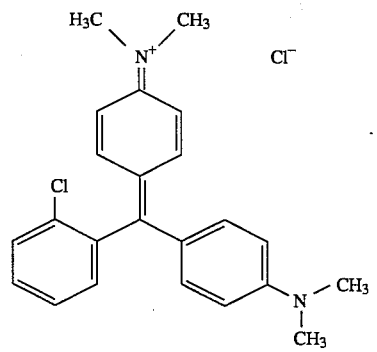
9. The process as claimed in claim 1, wherein the dye is
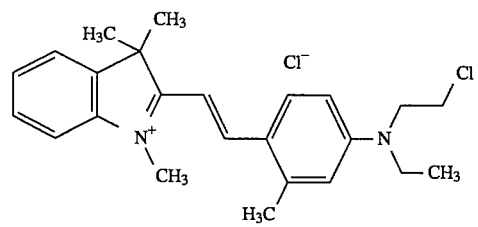
10. The process as claimed in claim 1, wherein the dye is
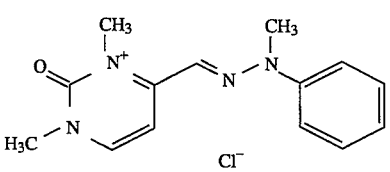
11. The process as claimed in claim 1, wherein the dye is
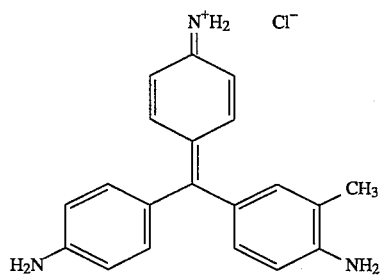
and
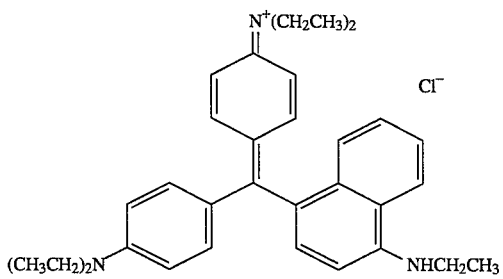
* * * * *